United States Patent
Ishibe (10) Patent No.: US 11,068,684 B2
(45) Date of Patent: Jul. 20, 2021

(54) FINGERPRINT AUTHENTICATION SENSOR MODULE AND FINGERPRINT AUTHENTICATION DEVICE

(71) Applicant: MICROMETRICS TECHNOLOGIES PTE. LTD., Singapore (SG)

(72) Inventor: Hiroshi Ishibe, Kyoto (JP)

(73) Assignee: MICROMETRICS TECHNOLOGIES PTE. LTD., Primz Bizhub (SG)

( * ) Notice: Subject to any disclaimer, the term of this patent is extended or adjusted under 35 U.S.C. 154(b) by 0 days.

(21) Appl. No.: 16/644,112

(22) PCT Filed: Sep. 5, 2017

(86) PCT No.: PCT/JP2017/031898
§ 371 (c)(1),
(2) Date: Mar. 3, 2020

(87) PCT Pub. No.: WO2019/049193
PCT Pub. Date: Mar. 14, 2019

(65) Prior Publication Data
US 2021/0064843 A1    Mar. 4, 2021

(51) Int. Cl.
*G06K 9/00*    (2006.01)
*G06K 9/20*    (2006.01)

(52) U.S. Cl.
CPC ....... *G06K 9/00013* (2013.01); *G06K 9/2027* (2013.01)

(58) Field of Classification Search
CPC .......................... G06K 9/00013; G06K 9/2027
See application file for complete search history.

(56) References Cited

U.S. PATENT DOCUMENTS 10,474,867 B2 * 11/2019 Yeke Yazdandoost ....................
H01L 51/5281
10,509,940 B2 * 12/2019 Yeke Yazdandoost ....................
G06K 9/2027

(Continued)

FOREIGN PATENT DOCUMENTS

EP    3147824 A1    3/2017
JP    10149446 A    6/1998

(Continued)

OTHER PUBLICATIONS

International Search Report issued in International Application No. PCT/JP2017/031898, dated Dec. 5, 2017, pp. 1-2, Japan Patent Office, Tokyo, Japan.

*Primary Examiner* — Utpal D Shah
(74) *Attorney, Agent, or Firm* — Hauptman Ham, LLP (57) ABSTRACT

To provide a fingerprint authentication sensor module having a simple configuration, high resolution, and a high authentication rate. A fingerprint authentication device includes a cover glass on which a finger is to be placed and a fingerprint authentication sensor module placed under the cover glass. The fingerprint authentication sensor module includes an image forming unit, a first glass portion placed under the image forming unit, and an image sensor placed under the first glass portion. The image forming unit includes an array of a plurality of microlenses and light-shielding portions that surround each of the plurality of microlenses and that limit light entering the array of the plurality of microlenses.

7 Claims, 7 Drawing Sheets

(56) References Cited

U.S. PATENT DOCUMENTS

| | | | |
|---|---|---|---|
| 2006/0155178 A1* | 7/2006 | Backman | G01N 33/48 600/315 |
| 2018/0012069 A1* | 1/2018 | Chung | G06K 9/2036 |
| 2018/0089491 A1* | 3/2018 | Kim | G06K 9/00912 |
| 2018/0301494 A1* | 10/2018 | Park | H01L 27/3234 |
| 2018/0349669 A1* | 12/2018 | Kim | G06K 9/22 |
| 2019/0012512 A1* | 1/2019 | He | G06K 9/0004 |
| 2019/0019000 A1* | 1/2019 | Lee | H01L 27/14678 |
| 2019/0171861 A1* | 6/2019 | Zhang | G06K 9/00026 |
| 2020/0380236 A1* | 12/2020 | He | G06K 9/00013 |

FOREIGN PATENT DOCUMENTS

| | | |
|---|---|---|
| JP | 2003006627 A | 1/2003 |
| JP | 2008165742 A | 7/2008 |
| JP | 2008168118 A | 7/2008 |
| JP | 2009511094 A | 3/2009 |
| JP | 2009165748 A | 7/2009 |
| JP | 2009238005 A | 10/2009 |
| JP | 2010035560 A | 2/2010 |
| JP | 2013236758 A | 11/2013 |
| WO | 2008004314 A1 | 12/2009 |

\* cited by examiner

FINGERPRINT AUTHENTICATION SENSOR MODULE AND FINGERPRINT AUTHENTICATION DEVICE

The present application is a National Phase of International Application Number PCT/JP2017/031898, filed Sep. 5, 2017, which is hereby incorporated by reference in its entirety.

TECHNICAL FIELD

The present invention relates to fingerprint authentication sensor modules and fingerprint authentication devices and more particularly to a high-resolution fingerprint authentication sensor module and a high-resolution fingerprint authentication device.

BACKGROUND ART

Fingerprint authentication devices for mobile terminals etc. are conventionally known in the art. Examples of such fingerprint authentication devices are described in European Patent Publication No. EP3147824 (Patent Literature 1) and Japanese Unexamined Patent Publication No. 2009-238005 (Patent Literature 2).

According to the fingerprint authentication device disclosed in Patent Literature 1, a finger is placed on a predetermined surface, and an image of the fingerprint is detected by an image sensor through a pinhole. Since an image is detected by the image sensor through the pinhole, an optical system can be simplified.

According to the fingerprint authentication device disclosed in Patent Literature 2, a fingerprint image is focused using a microlens array. In order to avoid degradation in image quality due to white light that does not contribute to vein recognition, near infrared light is selectively passed through an IR transmission filter and reaches a light receiving element. Resolution of captured data is thus improved as compared to conventional examples.

CITATION LIST

Patent Literatures

Patent Literature 1: European Patent Publication No. EP3147824 (Abstract etc.)
Patent Literature 2: Japanese Unexamined Patent Publication No. 2009-238005 (Abstract etc.)

SUMMARY OF INVENTION

Technical Problem

For example, in Patent Literature 1 of the above conventional fingerprint authentication devices, the optical system can be simplified, but resolution is poor as the fingerprint image is detected through the pinhole. Since there is no means for blocking disturbance light, sharpness and grayscale characteristics of the image are very poor. Moreover, since the finger is illuminated only by light emitted from the front, illumination is uneven and the fingerprint image is flat with fingerprint ridges and valleys not being three-dimensional. According to Patent Literature 2, the resolution is improved, but the configuration is complicated and therefore it costs more money.

The present invention was made in view of the above problems, and it is an object of the present invention to provide a fingerprint authentication device with a simple configuration and high resolution which is capable of producing a sharp image with excellent grayscale characteristics and which costs less money.

Solution to Problem

A fingerprint authentication sensor module according to the present invention includes: an image forming unit that focuses light from a fingerprint; and a detection module including a first glass portion placed under the image forming unit and an image sensor placed under the first glass portion. The image forming unit includes an array of a plurality of microlenses, and a light-shielding portion that surrounds each of the plurality of microlenses and that limits light entering the array of the plurality of microlenses.

Preferably, the light-shielding portion includes a light-shielding film surrounding each of the microlenses.

More preferably, the light-shielding portion includes a light-shielding dam having steps surrounding each of the microlenses.

The fingerprint authentication sensor module may further include an illumination device that illuminates the fingerprint. The illumination device may include a plurality of light sources, and the plurality of light sources may be able to be individually turned on and off, and brightness of the plurality of light sources may be able to be individually controlled.

The illumination device may be held by a holder substrate that positions the detection module or may be held by a peripheral wall that holds the detection module.

In another aspect of the present invention, a fingerprint authentication device includes the fingerprint authentication sensor module.

Advantageous Effects of Invention

The fingerprint authentication sensor module of the present invention is configured to use the microlenses and to shield portions other than a predetermined portion from light so that light other than light from the fingerprint to be obtained will not enter the microlenses. Accordingly, image data of a necessary portion is reliably obtained with high resolution.

High resolution fingerprint image data is thus obtained using a simple configuration. Due to the high resolution, a large amount of fingerprint information is obtained, which increases the authentication rate of the fingerprint authentication device.

DESCRIPTION OF EMBODIMENTS

Figure 1:
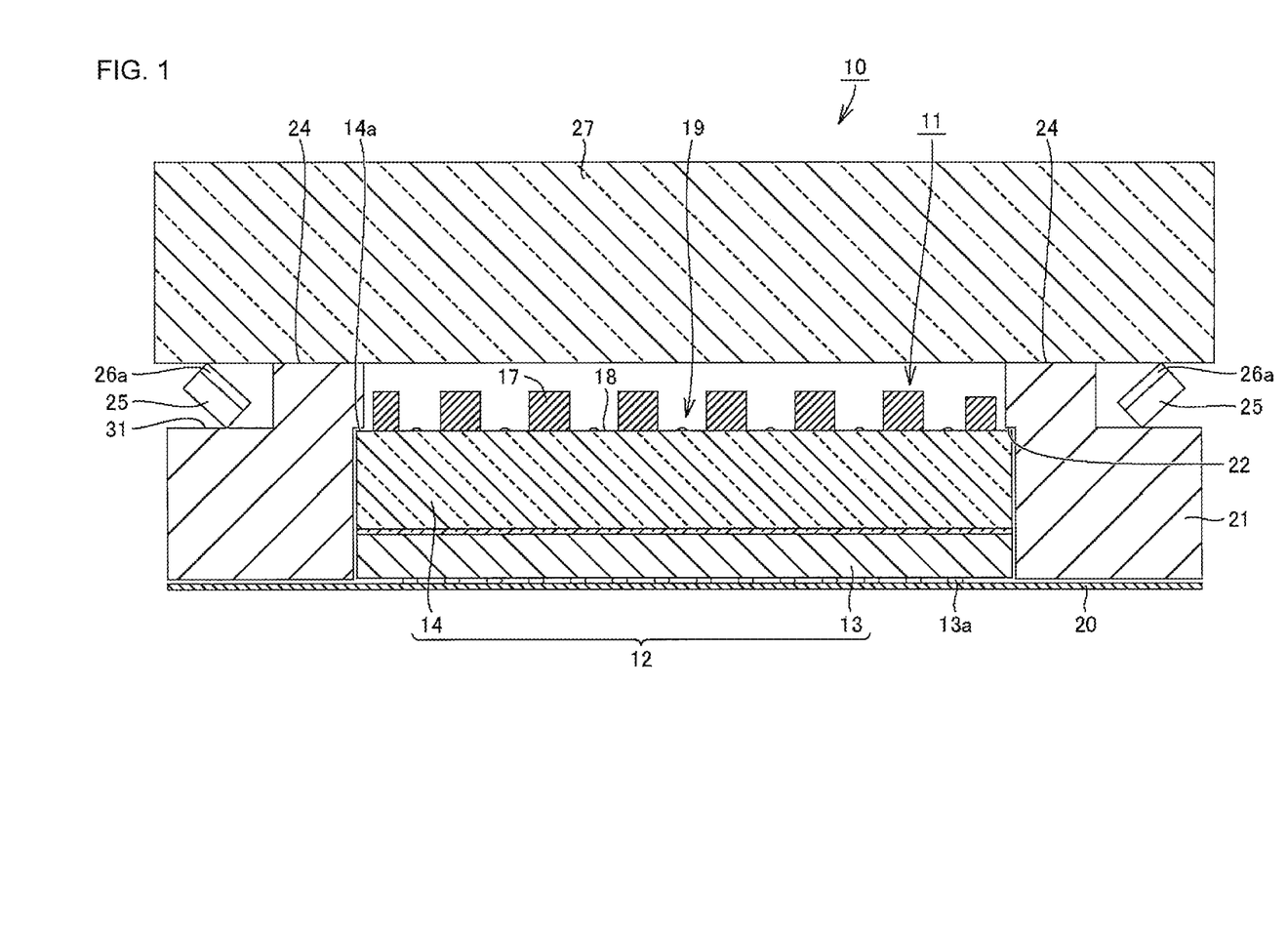
FIG. 1 is a sectional view of a fingerprint authentication device according to an embodiment of the present invention.
Figure 2:
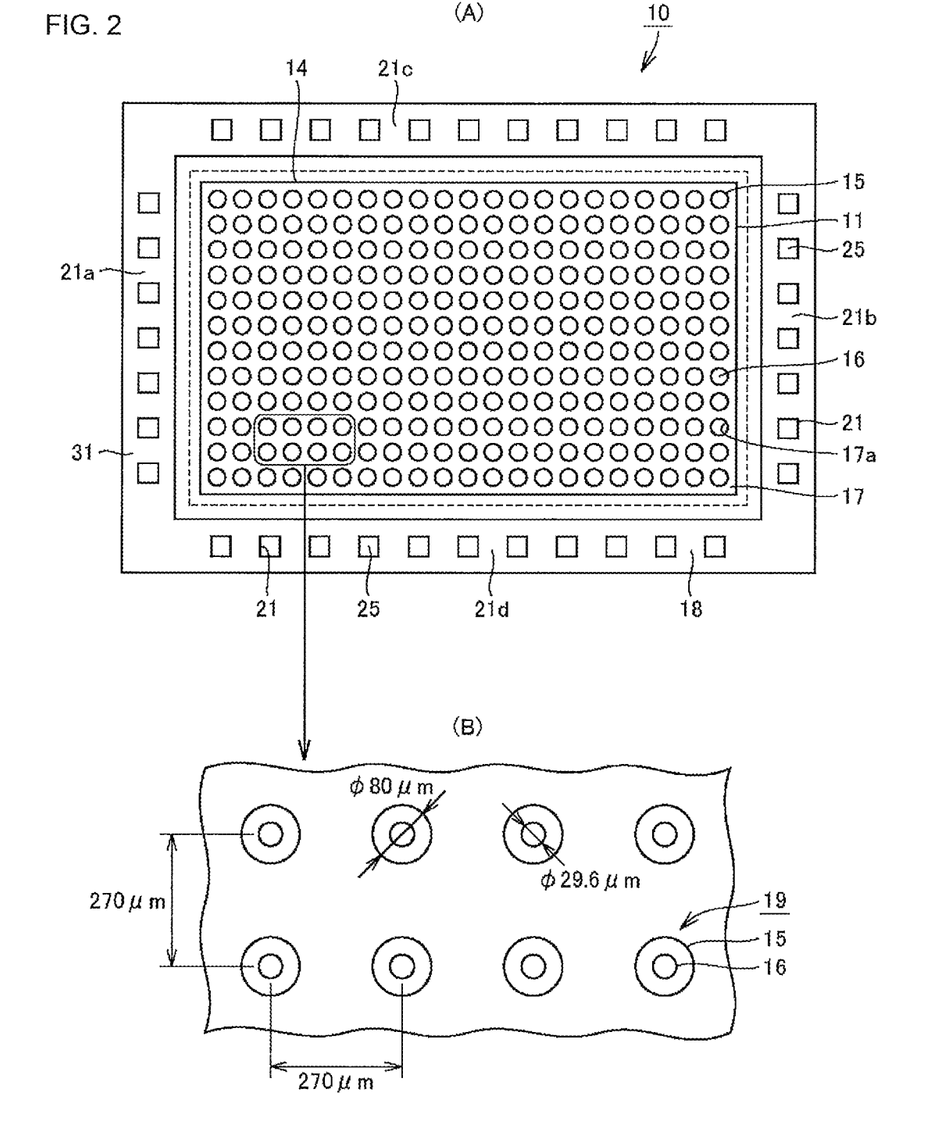
FIGS. 2A and 2B are plan views of the fingerprint authentication device according to the embodiment of the present invention.

Embodiments of the present invention will be described with reference to the accompanying drawings. FIG. 1 is a schematic sectional view of a fingerprint authentication device according to an embodiment of the present invention. FIG. 2A is a schematic plan view of the fingerprint authentication device shown in FIG. 1, and FIG. 2B is a schematic diagram illustrating a specific example of the dimensional relationship of a main part of the fingerprint authentication device.

Referring to FIGS. 1, 2A, and 2B, a fingerprint authentication device 10 includes a fingerprint authentication sensor module 11 and a cover glass 27 placed on the fingerprint authentication sensor module 11. The fingerprint authentication sensor module 11 includes: a flexible print circuit (FPC) board 20; an image sensor 13 that is connected to the FPC board 20 via lands 13a and that captures an image of a fingerprint; a transparent glass 14 (first glass) placed on the image sensor 13; and an image forming unit 19 that is placed on the transparent glass 14 and that collects light representing a fingerprint from a finger placed on the cover glass 27. The image forming unit 19 includes an array of a plurality of microlenses 16, a light-shielding member (hereinafter referred to as "light-shielding dam") 17 surrounding each of the plurality of microlenses 16 and having a predetermined height, and a thin light-shielding film 18 provided between each microlens 16 and the light-shielding dam 17. The microlenses 16 are preferably formed by printing.

As shown in FIG. 2B, the ratio of the interval in the vertical and horizontal directions between the microlenses 16, the diameter of openings 15 formed by the light-shielding dam 17, and the diameter of the microlenses 16 are preferably approximately 1:0.3:0.1.

As an example, in the present embodiment, the microlenses 16 are arranged at intervals of 270 μm in the vertical and horizontal directions, the diameter of the openings 15 formed by the light-shielding dam 17 is about 80 μm, and the diameter of the microlenses 16 is about 29.6 μm.

The image sensor 13 and the transparent glass 14 placed thereon are in the shape of a rectangular parallelepiped having the same planar dimensions (these are together referred to as a detection module 12).

A method for assembling the fingerprint authentication sensor module 11 will be described. First, the detection module 12 composed of the image sensor 13 and the transparent glass 14 placed thereon is prepared. The image forming unit 19 is formed on the detection module 12. In order to hold the detection module 12 having the image forming unit 19 formed thereon, the detection module 12 is surrounded by a holder substrate 21. The FPC board 20 is then attached to the image sensor 13 by soldering via the lands 13a. Thereafter, the cover glass 27 is attached to an upper end 24 of the holder substrate 21 with glue etc. The fingerprint authentication device is thus completed.

A specific method for holding the detection module 12 will be described. The four sides of an upper end of the transparent glass 14 have corners 14a. The holder substrate 21 is shaped to have a rectangular parallelepiped cavity in the center which can accommodate the image sensor 13 and the transparent glass 14. The cavity has a step 22 that divides the cavity into upper and lower parts. The opening area of the upper part of the cavity is smaller than that of the lower part of the cavity. As the step 22 presses the corners 14a of the transparent glass 14, the image sensor 13 and the transparent glass 14 are positioned by the holder substrate 21.

The holder substrate 21 has four sides, and the right, left, upper, and lower sides of the holder substrate 21 are herein denoted by 21b, 21a, 21c, 22d, respectively, for convenience. The upper end 24 of the holder substrate 21 is located higher the image forming unit 19 provided on the transparent glass 14. In the present embodiment, a space containing air is present between the transparent glass 14 and the cover glass 27 in the holder substrate 21.

The cover glass 27 on which a human finger is to be placed is disposed on the upper end 24 of the holder substrate 21.

The holder substrate 21 has a step 31 along the outer periphery of the upper end 24, and LEDs 25 that emit light to the fingerprint of a finger placed on the cover glass 27 are disposed on the step 31. As shown in FIG. 2A, a plurality of LEDs 25 are arranged at certain intervals on each side 21a to 21d of the holder substrate 21.

Next, the image forming unit 19 will be described. As shown in FIGS. 2A and 2B, the plurality of microlenses 16 are arranged in an array and each microlens 16 is surrounded by the light-shielding dam 17 having cylindrical inner wall surfaces 17a. The light-shielding dam 17 therefore has the plurality of circular openings 15 formed in an array as viewed from above. This will be described in detail with reference to FIG. 3.

Figure 3:
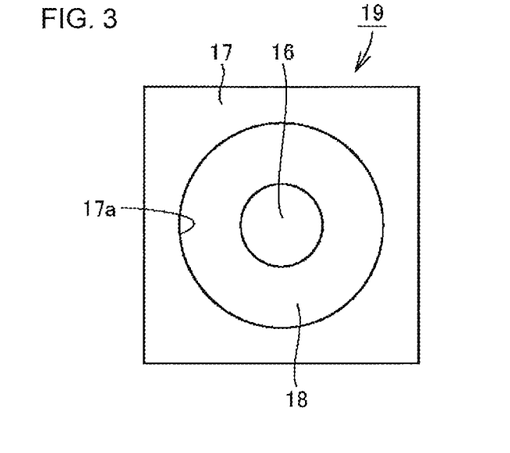
FIG. 3 is a plan view of a main part of FIG. 2A.

FIG. 3 is a plan view illustrating in detail an area around one microlens 16 of the fingerprint authentication device shown in FIG. 2A. Referring to FIG. 3, the microlens 16 is located in the center of the circular opening 15 of the light-shielding dam 17, and the region between the inner wall surface 17a of the light-shielding dam 17 and the microlens 16 is covered by the light-shielding film 18.

An illumination device using the LEDs 25 will be described. As shown in FIGS. 1 and 2A, the LEDs 25 as an illumination device are arranged at certain intervals on the four sides (21a to 21d) of the holder substrate 21. The LEDs 25 can be individually turned on and off and brightness of the LEDs 25 can be individually controlled. Tilting of the optical axes of the LEDs 25 is individually controlled by a control unit, not shown. Light that is most suitable for imaging can thus be directed to the fingerprint. In this example, a diffuser 26a that diffuses light is placed in front of each LED 25. However, the diffuser 26a may be omitted.

The direction in which light is emitted to the fingerprint can be controlled by controlling the optical axes of the LEDs 25. For example, only the LEDs 25 located on both sides of the fingerprint (in FIG. 2A, a pair of LEDs 25 arranged in the vertical direction or a pair of LEDs 25 arranged in the horizontal direction) are turned on to obliquely emit light to the fingerprint, whereby a three-dimensional image can be produced. Fingerprint ridges and sweat glands can thus be shot, which increases fingerprint authentication accuracy.

Only one or more of the plurality of LEDs 25 which are located at a desired position(s) may be selectively turned on in order to obtain a three-dimensional fingerprint image.

Figure 4:
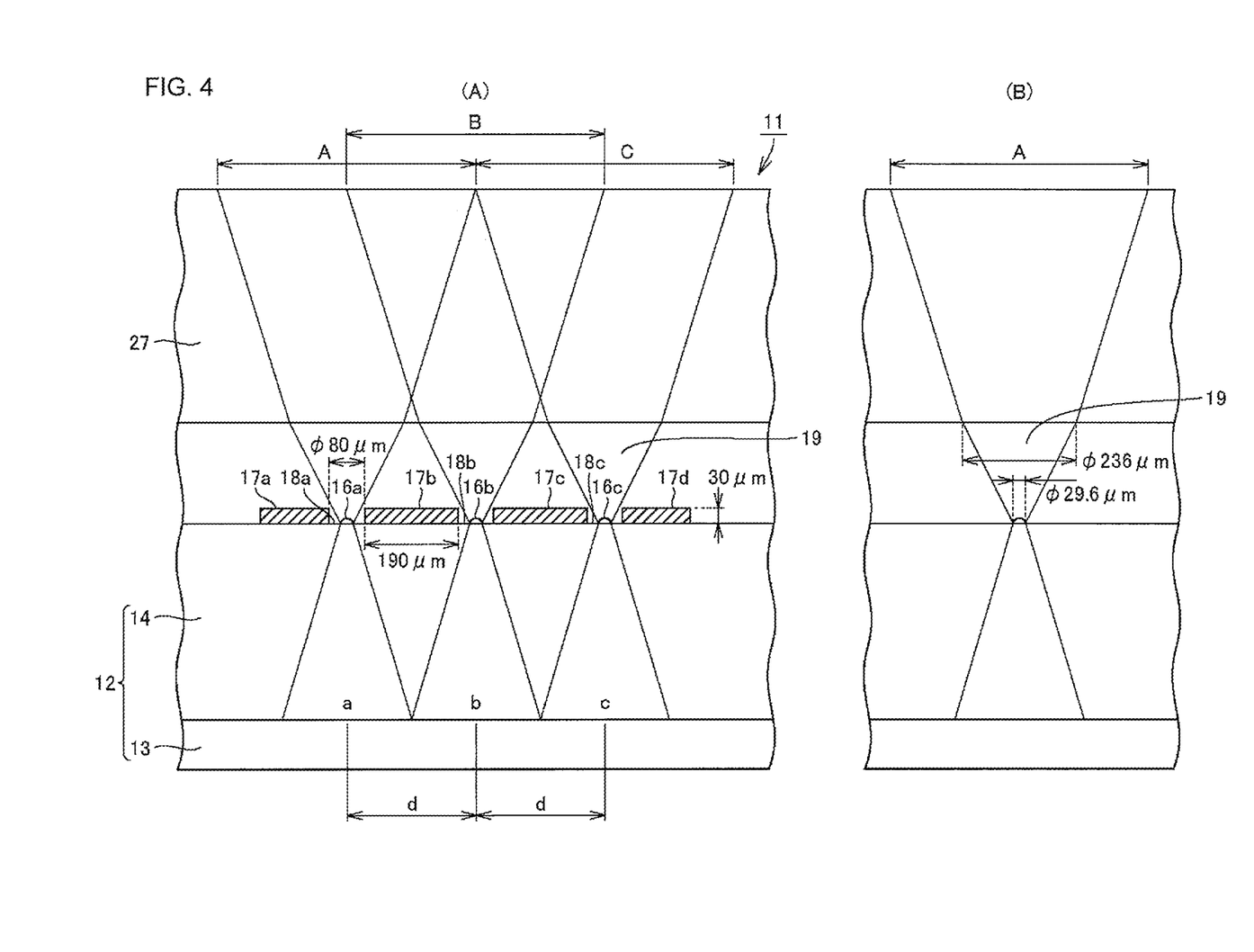
FIGS. 4A and 4B illustrate an optical system of the fingerprint authentication device.

An optical system of the microlenses 16 will be described with reference to a section of the configuration. FIGS. 4A and 4B illustrate an optical system in which the fingerprint projected onto the image sensor 13 by a plurality of microlenses 16 (in this example, three microlenses 16). FIG. 4A illustrates an optical system of three microlenses 16 whose subject portions overlap each other, and FIG. 4B illustrates an optical system of one microlens 16. Referring to FIGS.

4A and 4B, the plurality of microlenses 16 are arranged at intervals d (270 μm) in the vertical and horizontal directions as described above as an example. Light reflected from an image of a portion A of the fingerprint on the cover glass 27 and passed through a microlens 16a of the fingerprint authentication sensor module 11 is projected on a portion a of the image sensor 13 through the transparent glass 14, and the projected image is captured. Similarly, an image of a portion B is projected on a portion b, and an image of a portion C is projected on a portion c. An image of the fingerprint is thus captured. The portions A, B, and C have the same diameter (540 μm as described later).

In order to define the lens shape on the image sensor 13, the microlenses 16a, 16b, and 16c are surrounded by light-shielding films 18a, 18b, and 18c for blocking light, respectively. Since the light-shielding films 18a, 18b, and 18c are present, disturbance light that does not pass through the microlens array is blocked. Light is therefore less likely to enter from portions other than necessary portions. Since the microlenses 16a, 16b, and 16c are individually separated from each other by light-shielding dams 17a to 17d, light from the fingerprint image other than the portions A, B, and C is not collected by the microlenses 16a, 16b, and 16c, respectively. Only specific portions of the fingerprint image are thus captured by specific pixels of the image sensor 13. As a result, the entire fingerprint image is reliably captured.

An example in which the light-shielding film and the light-shielding dam surround the individual microlenses in order to limit light entering the microlenses is described above. However, the present invention is not limited to this example. A funnel-shaped shielding dam may be formed which has openings each having an upper edge corresponding to the upper end of the opening dimension of the light-shielding dam (the inner wall surface 17a of the light-shielding dam 17 shown in FIG. 3) and a lower edge corresponding to the lower end of the outer peripheral dimension of the microlens.

In the case where the microlenses 16 are formed by printing as described above with a height of about 1 μm on the transparent glass 14, the light-shielding film 18 is formed by printing in the subsequent step with a height of about 1 μm on the regions of the transparent glass 14 where the microlenses 16 are not present.

Cost reduction and improvement in manufacturing accuracy are achieved by forming the microlenses etc. by printing.

Next, resolution of the fingerprint authentication device 10 of the present embodiment will be described. Specifically, as an example, a finger was placed on the cover glass 27, and images of the finger were captured at a reduction factor of ½ on the image sensor 13 with 1920 pixels by 1080 pixels. The images were reconstructed, and resolution of the resultant image was calculated. In the case where the dimensions of one pixel are 3 μm, the horizontal dimension is 1920×3=5760 μm and the vertical dimension is 1080×3=3240 μm.

Image reconstruction herein means that many images of the finger are captured in the vertical and horizontal directions and combined into a single image. Specifically, the output of the image sensor 13 is processed by a processor, not shown, using a predetermined program to produce an image with 1:1 correspondence to that of the fingerprint authentication device 10.

Figure 5:
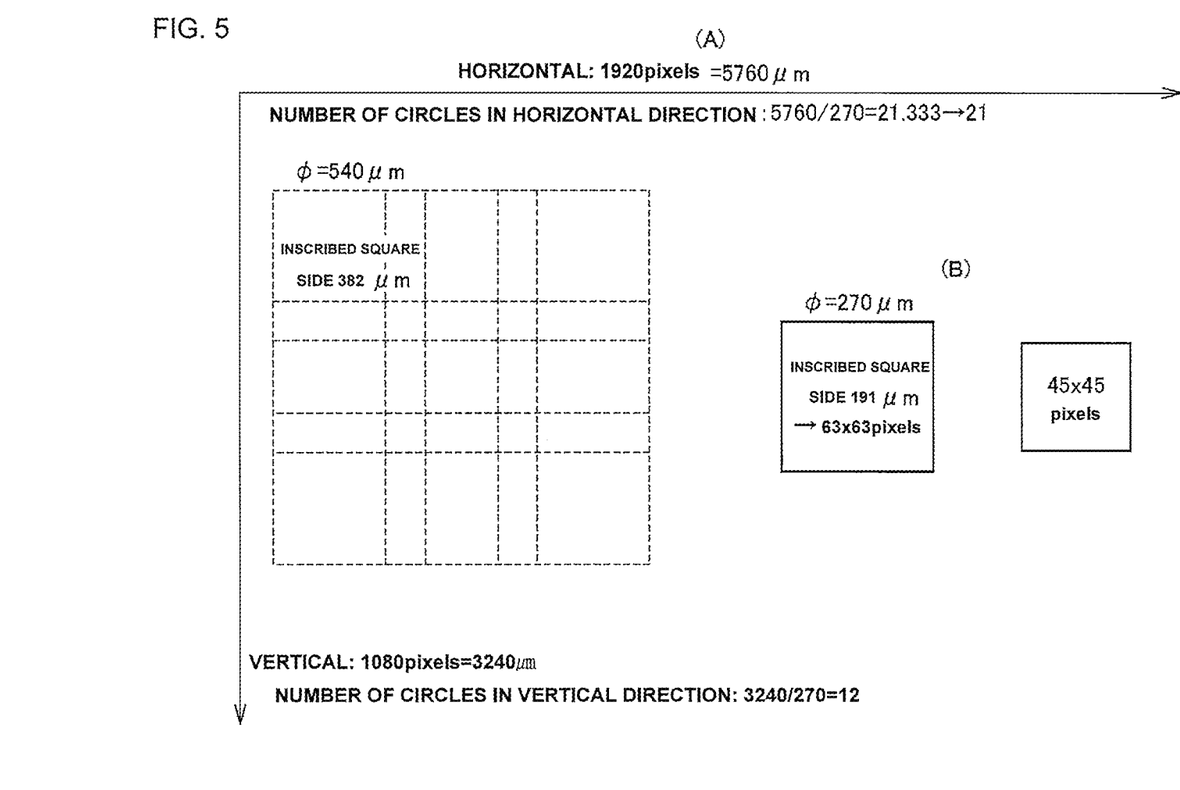
FIGS. 5A and 5B illustrate resolution of the fingerprint authentication device according to the present invention.

FIG. 5A illustrates calculation of the imaging range on the cover glass 27, and FIG. 5B illustrates the state of image information that is obtained to reconstruct images formed on the image sensor 13 through the microlenses 16.

As shown in FIG. 5A, the imaging range (image circle) on the cover glass 27 is a circle with a diameter of 540 μm. A square inscribed in the circle has a side of $540/\sqrt{2}=381.84$ μm, and inscribed squares that do not overlap each other have a side of 540/2=270 μm. The horizontal dimension of the imaging range of a figure is approximately the same as the horizontal dimension of the image sensor 13, namely 5760 μm, and the vertical dimension of the imaging range of a finger is also approximately the same as the vertical dimension of the image sensor 13, namely 3240 μm.

Regarding images formed on the image sensor 13, as shown in FIG. 5B, since the image circle on the image sensor 13 has a diameter of 270 μm, a square inscribed in the circle has a side of $270/\sqrt{2}=190.92$ μm, and the number of pixels on each side of the square is 190.92/3=63.64 pixels, namely about 63 pixels. Inscribed squares that do not overlap each other have a side of 270/2=135 μm, and the number of pixels on each side of the square is 135/3=45 pixels.

The number of pixels after reconstruction is 45×21+30=975 in the horizontal direction and 45×12=540 in the vertical direction.

Although it varies depending on the lens capability, the resolution is 975 pixels/5760 μm×25400 μm according to the calculations, which means that the resolution can be 4300 pixels/inch. This value is more than five times the resolution of common fingerprint authentication devices which is 800 pixels/inch.

As described above, in the present embodiment, the light-shielding dam and the light-shielding film are provided so as to separate each microlens that collects light from a specific image of a fingerprint from the other microlenses. An image of a specific portion of the fingerprint can thus be reliably obtained.

As a result, a sharp fingerprint image with a higher resolution can be obtained.

Figure 6:
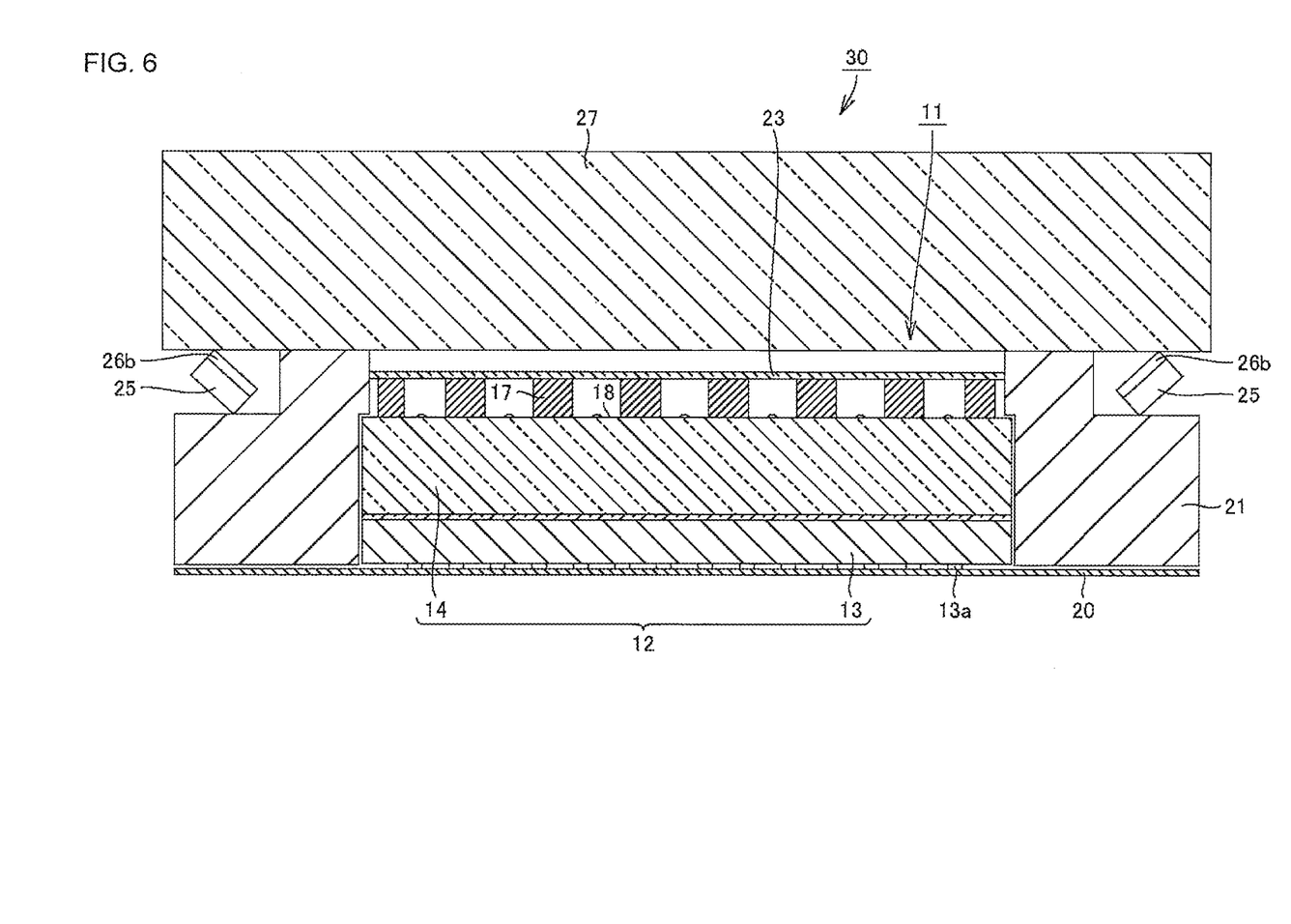
FIG. 6 is a sectional view of a fingerprint authentication device according to another embodiment of the present invention.

Another embodiment of the present invention will be described. FIG. 6 is a diagram corresponding to FIG. 1 of the above embodiment, illustrating a fingerprint authentication device 30 according to another embodiment of the present invention.

Referring to FIG. 6, the fingerprint authentication device 30 of the present embodiment basically has a structure similar to that of the above embodiment. The difference is that, in the above embodiment, the diffuser 26a is placed in front of the light-emitting portion on the front end of each LED 25, but in the present embodiment, a polarizing filter 26b is provided instead of the diffuser 26a and a polarizing filter 23 that operates cooperatively with the polarizing filters 26b is placed on top of the light-shielding dam 17. With this configuration, a clearer image can be obtained by the image sensor 13. Even by merely placing the polarizing filter 26b in front of the light emitting portion, a sharper image can be obtained as waves of illumination light passed through the polarizing filter 26b oscillate in one direction.

Since the present embodiment otherwise has the same configuration as the above embodiment, the same portions are denoted with the same reference characters as those of the above embodiment and description thereof is omitted.

Figure 7:
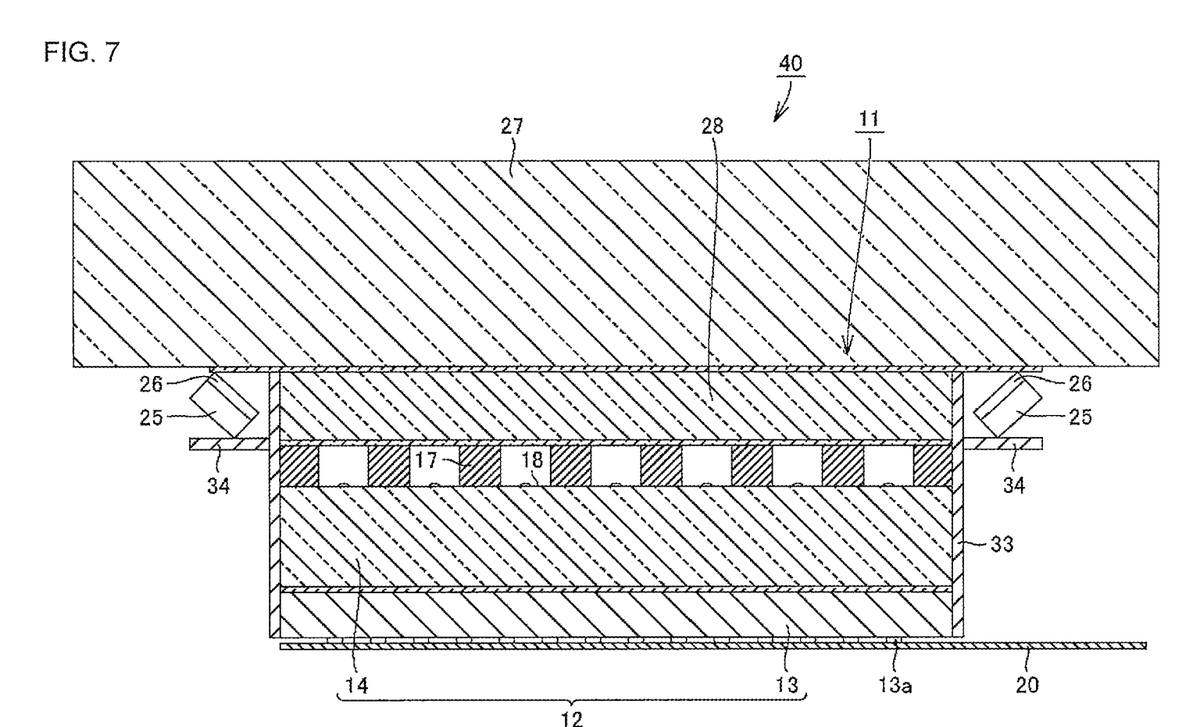
FIG. 7 is a sectional view of a fingerprint authentication device according to still another embodiment of the present invention.

Next, still another embodiment of the present invention will be described. FIG. 7 is a diagram corresponding to FIG. 1 of the first embodiment, illustrating a fingerprint authentication device 40 according to still another embodiment of the present invention.

Referring to FIG. 7, the fingerprint authentication device 40 according to the present embodiment basically has a structure similar to that of the first embodiment. The difference is that, in the first embodiment, the step of the holder substrate is used to position the image sensor 13 etc., but in the present embodiment, a second transparent glass 28 is placed on top of the image forming unit 19 provided above the image sensor 13 such that the second transparent glass 28 is supported by the top part of the light-shielding dam 17.

In this case, transparent glue 29 may be applied between the second transparent glass 28 and the light-shielding dam 17. Moreover, in this case, the components from the image sensor 13 to the second transparent glass 28 placed above the image sensor 13 have the same planar dimensions. Accordingly, a peripheral wall 33 surrounding these components is provided, and a plurality of LEDs 25 are arranged around the upper end of the peripheral wall 33.

In the first embodiment, the LEDs 25 are provided on the holder substrate 21. In the present embodiment, however, no holder substrate is provided, and a support 34 for supporting the LEDs 25 is provided on the peripheral wall 33 surrounding the image sensor 13 and the transparent glass 14. Since the present embodiment otherwise has the same configuration as the first embodiment, the same portions are denoted with the same reference characters as those of the first embodiment and description thereof is omitted.

The thickness of the second transparent glass 28 is about 200 µm, and the fingerprint authentication device 40 has a smaller overall thickness due to the refractive index of the second transparent glass 28. However, the planar dimensions of each component of the present embodiment are basically the same as those of the first embodiment.

In the present embodiment, a step etc. for positioning need not be formed as in the first embodiment. Accordingly, the configuration is simplified, and mass production efficiency is improved.

Next, further advantageous effects of the present invention will be described.

In the present embodiment, the f-number is about 9.0 and the focal length of the microlenses 16 is 179.25 µm when the fingerprint authentication device 40 has the following specifications. The diameter of the image circle on the cover glass 27 for detecting an image of a finger is 540 µm, the image forming plane size is 270 µm, the diameter of the microlenses 16 is 30 µm, the refractive index of the transparent glass 14 is about 1.5, the thickness of the transparent glass 14 is 400 µm, and the thickness of the cover glass 27 is 500 µm.

As a result, on the assumption that the lens capability satisfies 2540 dpi, the front depth of field (from the position of the fingerprint toward the microlens 16) is about 380 µm, the rear depth of field (from the position of the fingerprint toward the opposite side from the microlens 16) is about 890 µm, and the depth of focus at the image forming plane is about ±150 µm.

An image that satisfies predetermined performance is thus obtained in a contactless manner without touching the cover glass 27 with a finger.

Moreover, a three-dimensional image can be obtained by capturing an image through a plurality of lenses.

In the above embodiments, an example is described in which each of the microlenses 16 arranged in a grid pattern is surrounded by the light-shielding dam 17 formed in a grid pattern. However, the present invention is not limited to this. The microlenses 16 may be arranged in a honeycomb pattern and the light-shielding dam 17 may be formed in a honeycomb pattern. This configuration increases the usage ratio of the pixels of the image sensor 13 and thus improves resolution.

In the above embodiments, an illumination method using LEDs is described. However, the present invention is not limited to this. A planar LED or an organic EL may be placed over the entire light-shielding dam. In this configuration, the light emitting surface faces upward. A finger can thus be illuminated through the cover glass. Specifically, an organic EL having holes with a diameter of 80 µm is placed over the light-shielding dam as viewed from above.

Since the organic EL is used, brightness of any part of the planar illumination device is easily increased or reduced as desired.

In the case where the fingerprint authentication sensor module provided with the organic EL is increased in size to the shape of a mobile terminal, the entire display portion of the mobile terminal has the fingerprint authentication sensor module as the fingerprint authentication sensor module itself incudes the organic EL. Accordingly, the fingerprint can be authenticated no matter which part of the display portion of the mobile terminal is touched. When a finger is placed on the display portion of the mobile terminal, an image of the finger can be stored in a memory, not shown.

Although the embodiments of the present invention are described above with reference to the drawings, the present invention is not limited to the illustrated embodiments. Various changes and modifications can be made to the illustrated embodiments without departing from the spirit and scope of the invention.

INDUSTRIAL APPLICABILITY

The fingerprint authentication device according to the present invention has a simple configuration and produces high resolution fingerprint image data. The fingerprint authentication device according to the present invention thus has an improved authentication rate and is advantageously used as a fingerprint authentication device.

REFERENCE SIGNS LIST 10, 30, 40: Fingerprint Authentication Device, 11: Fingerprint Authentication Sensor Module, 12: Detection Module, 13: Image Sensor, 14: Transparent Glass, 14a: Corner, 15: Opening, 16: Microlens, 17: Light-Shielding Dam, 18; Light-Shielding Film, 19: Image Forming Unit, 20: FPC Board, 21: Holder Substrate, 22: Step, 23: Polarizing Filter, 25: LED, 26: Diffuser, 27: Cover Glass, 28: Second Transparent Glass, 29: Transparent Glue, 33: Peripheral Wall, 34: Support

The invention claimed is:

1. A fingerprint authentication sensor module, comprising:
an image forming unit that focuses light from a fingerprint; and
a detection module including a first glass portion placed under the image forming unit and an image sensor placed under the first glass portion, wherein
the image forming unit includes
an array of a plurality of microlenses, and
a light-shielding portion that surrounds each of the plurality of microlenses and that limits light entering the array of the plurality of microlenses,
wherein a height of the microlenses with respect to the image sensor is less than a height of the light-shielding portion with respect to the image sensor such that the microlenses are within a cavity defined by the light-shielding portion.

2. The fingerprint authentication sensor module according to claim 1, wherein
the light-shielding portion includes a light-shielding film surrounding each of the microlenses.

3. The fingerprint authentication sensor module according to claim 1, wherein
the light-shielding portion includes a light-shielding dam having steps surrounding each of the microlenses.

4. The fingerprint authentication sensor module according to claim 1, further comprising:
an illumination device that illuminates the fingerprint, wherein
the illumination device includes a plurality of light sources, and
the plurality of light sources can be individually turned on and off, and brightness of the plurality of light sources can be individually controlled.

5. The fingerprint authentication sensor module according to claim 4, further comprising:
a holder substrate that positions the detection module, wherein
the holder substrates holds the illumination device.

6. The fingerprint authentication sensor module according to claim 4, further comprising:
a peripheral wall that holds the detection module, wherein
the peripheral wall holds the illumination device.

7. A fingerprint authentication device, comprising the fingerprint authentication sensor module according to claim 1.

* * * * *